US007648065B2

(12) United States Patent  
Marino

(10) Patent No.: US 7,648,065 B2
(45) Date of Patent: Jan. 19, 2010

(54) STORAGE CABINET WITH IMPROVED RFID ANTENNA SYSTEM

(75) Inventor: Ronald A. Marino, Jackson, NJ (US)

(73) Assignee: The Stanley Works, New Britain, CT (US)

( * ) Notice: Subject to any disclaimer, the term of this patent is extended or adjusted under 35 U.S.C. 154(b) by 236 days.

(21) Appl. No.: 11/456,275

(22) Filed: Jul. 10, 2006

(65) Prior Publication Data

US 2007/0046552 A1    Mar. 1, 2007

Related U.S. Application Data

(60) Provisional application No. 60/713,545, filed on Aug. 31, 2005.

(51) Int. Cl.
*G06K 15/00* (2006.01)

(52) U.S. Cl. .................................. 235/383; 235/492

(58) Field of Classification Search ................ 235/492, 235/449, 380, 382, 486, 383; 428/195.1; 340/572.1

See application file for complete search history.

(56) References Cited

U.S. PATENT DOCUMENTS

| | | | |
|---|---|---|---|
| 4,679,046 A | 7/1987 | Curtis et al. | |
| 6,020,856 A | 2/2000 | Alicot | |
| 6,069,564 A | 5/2000 | Hatano | |
| 6,335,686 B1 | 1/2002 | Goff | |
| 6,392,544 B1 | 5/2002 | Collins | |
| 6,407,665 B2 | 6/2002 | Maloney | |
| 6,445,297 B1 | 9/2002 | Nicholson | |
| 6,707,380 B2 | 3/2004 | Maloney | |
| 6,720,930 B2 | 4/2004 | Johnson | |
| 6,753,821 B2 | 6/2004 | Yang | |
| 6,812,838 B1 | 11/2004 | Maloney | |
| 6,861,993 B2 | 3/2005 | Waldner | |
| 6,903,656 B1 | 6/2005 | Lee | |
| 6,943,688 B2 | 9/2005 | Chung | |
| 6,956,538 B2 | 10/2005 | Moore | |
| 6,963,317 B2 | 11/2005 | Zuk | |
| 6,989,796 B2 | 1/2006 | Rahim | |
| 7,145,590 B2 * | 12/2006 | Takagi et al. | 347/244 |
| 7,378,836 B2 * | 5/2008 | Teoh et al. | 324/158.1 |
| 2003/0141962 A1 | 7/2003 | Barink | |
| 2004/0100413 A1 * | 5/2004 | Waldner | 343/742 |
| 2004/0212542 A1 | 10/2004 | Rahim | |
| 2004/0224135 A1 * | 11/2004 | Krebs | 428/195.1 |
| 2005/0006569 A1 * | 1/2005 | Yoshiyuki | 250/221 |
| 2005/0189370 A1 * | 9/2005 | Carter et al. | 221/123 |
| 2008/0266092 A1 * | 10/2008 | Campero et al. | 340/572.1 |

* cited by examiner

*Primary Examiner*—Thien M Le
(74) *Attorney, Agent, or Firm*—Pillsbury Winthrop Shaw Pitman LLP

(57) ABSTRACT

A system for reading RFID tags of articles within a cabinet includes a repositionable shelf. The repositionable shelf includes an antenna assembly having three antenna pairs. Each antenna pair has a loop antenna and a figure eight antenna. The antenna pairs are on a PC board. The PC board includes an RJ45 connector which provides both power to the antenna assembly as well as a communication interface for the antenna assembly. The RJ45 connector could be used to provide the RF signals from the antenna to a reader. The system could also include a repositionable divider for placement perpendicular to the repositionable shelf. The repositionable divider also includes a loop antenna and a figure eight antenna.

10 Claims, 10 Drawing Sheets

STORAGE CABINET WITH IMPROVED RFID ANTENNA SYSTEM

PRIORITY CLAIM

This application claims priority from U.S. Provisional Application No. 60/713,545, filed Aug. 31, 2005, entitled "RFID Shelf Incorporating Planar Complementary Antennas".

BACKGROUND OF THE INVENTION

This invention relates to item tracking systems and inventory management and more particularly to an antenna assembly for use with an RFID tracking system.

"Smart shelves" refer to systems used to identify articles equipped with a radio frequency identification (RFID) transponder, or "tag". Smart shelf systems are capable of determining the number, identity, and location of RFID tagged items placed on a store shelf, book shelf, or in a cabinet. When these shelves or other fixtures are equipped with one or more antennas coupled to an RFID interrogator, the contents of an article's tag may be read by the RFID interrogator. The number and location of each article may then be obtained and the location and use of the article tracked. Out of stock situations may be avoided and reordering of articles may also be handled automatically based upon information from the system.

RFID antenna systems for use with shelf systems have unique design specifications. Antenna systems must be designed to obtain information from RFID tags within a limited area. The antenna systems should not read RFID tags from adjacent shelves.

Because an RFID antenna system within a shelf is to be effective within a relatively small area, traditional "far field" analysis of the antenna systems is not useful. Rather, coverage by the RFID antenna with the "near field" of approximately zero to sixteen inches from the antenna system must be optimized.

As is well known, antennas have dead zones, referred to generally as nulls. Objects placed in a null of an antenna will not couple with the antenna. If complete coverage for an area is required, multiple antennas must be used. Multiple antennas, however, present an additional problem. Antennas in close proximity couple, thereby creating additional nulls. This is especially problematic in the near field since the coupling between the antennas can be particularly strong.

One use of smart shelves is to track medical supplies having RFID tags. Some medical supplies are extremely expensive, costing several thousand dollars per item. The medical supplies are often used at the medical facility, and their use may be billed to a particular patient. Thus, maintaining an accurate inventory and location of expensive medical supplies is important.

Medical RFID systems previously proposed are expensive, involving elaborate storage containers made specifically for scanning RFID equipped articles. The containers cannot be easily adjusted to accommodate different size articles. Additionally, the RFID systems are not easily moved from one location to another. Further, the accuracy of current RFID systems for use in medical facilities is less than desirable.

Thus, an improved antenna system for tracking articles stored within a cabinet or shelving system is highly desirable.

SUMMARY OF THE INVENTION

The aforementioned problems are overcome by a moveable and reconfigurable storage device using an RFID antenna system utilizing multiple instances of a figure eight antenna in combination with a loop antenna. In a preferred embodiment, the loop antenna and the figure eight antenna are arranged about a common axis, referred to as the X-axis. The figure eight antenna is placed symmetrically within the loop antenna.

Currents created in one part of the figure eight antenna due to coupling with the loop antenna are offset by equal and opposite current created in another portion of the figure eight antenna. Similarly, currents created within the loop antenna due to coupling with one portion of the figure eight antenna are countered by equal and opposite currents created by coupling with another portion of the figure eight antenna. Thus, nulls created by the coupling between the figure eight antenna and the loop antenna are substantially reduced. Since the nulls between the two antennas are minimized, it is possible to place the two antennas in relatively close proximity, thereby allowing the near-field coverage of the two antennas to be maximized.

To further improve the accuracy and detection of the antenna assembly, an additional antenna is arranged such that the axis about which it is aligned, refereed to as the Y-axis, is aligned generally perpendicular to that of the X-axis. Additional antennas having axes parallel to the X-axis and perpendicular to the Y-axis may also be provided.

Additional instances of the combination of a loop antenna with a figure eight antenna placed in the same plane as the initial combination and having an axis parallel to the X-axis provide even greater accuracy.

The resultant antenna assembly has few nulls and allows for highly accurate detection and reading of RFID tags. The antenna assembly can be manufactured on a single printed circuit (PC) board by placing multiple instances of the loop antenna within the figure eight antenna on one side of the PC board. The other side of the PC board includes antennas arranged so that their axes are parallel to the Y-axis.

In the current embodiment, the antenna assembly has a layer with several coplanar antennas on side of the PC board. The first antenna layer has a loop antenna enclosing a first figure eight antenna. A second figure eight antenna is positioned within the perimeter of the first loop of the first figure eight antenna. Within the second figure eight antenna is a second loop antenna. A third figure eight antenna is positioned within the perimeter of the second loop of the first figure eight antenna. A third loop antenna is positioned within the perimeter of the third figure eight antenna.

To improve the manufacturability of the PC board, the width of the antenna elements of the first antenna pair is larger than the width of the antenna elements of the second antenna pair or the third antenna pair, thereby providing that the inductance of each of the antennas is approximately the same. Since the inductance of the antennas is approximately the same, the same size tuning capacitors for each antenna can be used.

The antenna assembly can be enclosed within a shelf. The shelf can be moveably repositioned within a cabinet, thereby allowing the cabinet to accommodate a variety of different sized articles. Further, if it is desired for the cabinet to hold different sized articles at a later time, the shelves can be easily and quickly repositioned. If the connector for the antenna assembly supplies power to the antenna assembly and provides data and RF connectivity for the antenna assembly, then the ease of moving the shelves is even further accentuated in that only a single connector need be connected or disconnected whenever the shelf is moved.

The resultant system has high accuracy detecting RFID tagged items placed on the shelf. Additionally, the shelves are easily movable, allowing a cabinet or shelf system to be adaptable so as accommodate a variety of articles.

These and other objects, advantages, and features of the invention will be more fully understood and appreciated by reference to the description of the current embodiment and the drawings.

DESCRIPTION OF THE CURRENT EMBODIMENT

Figure 1:
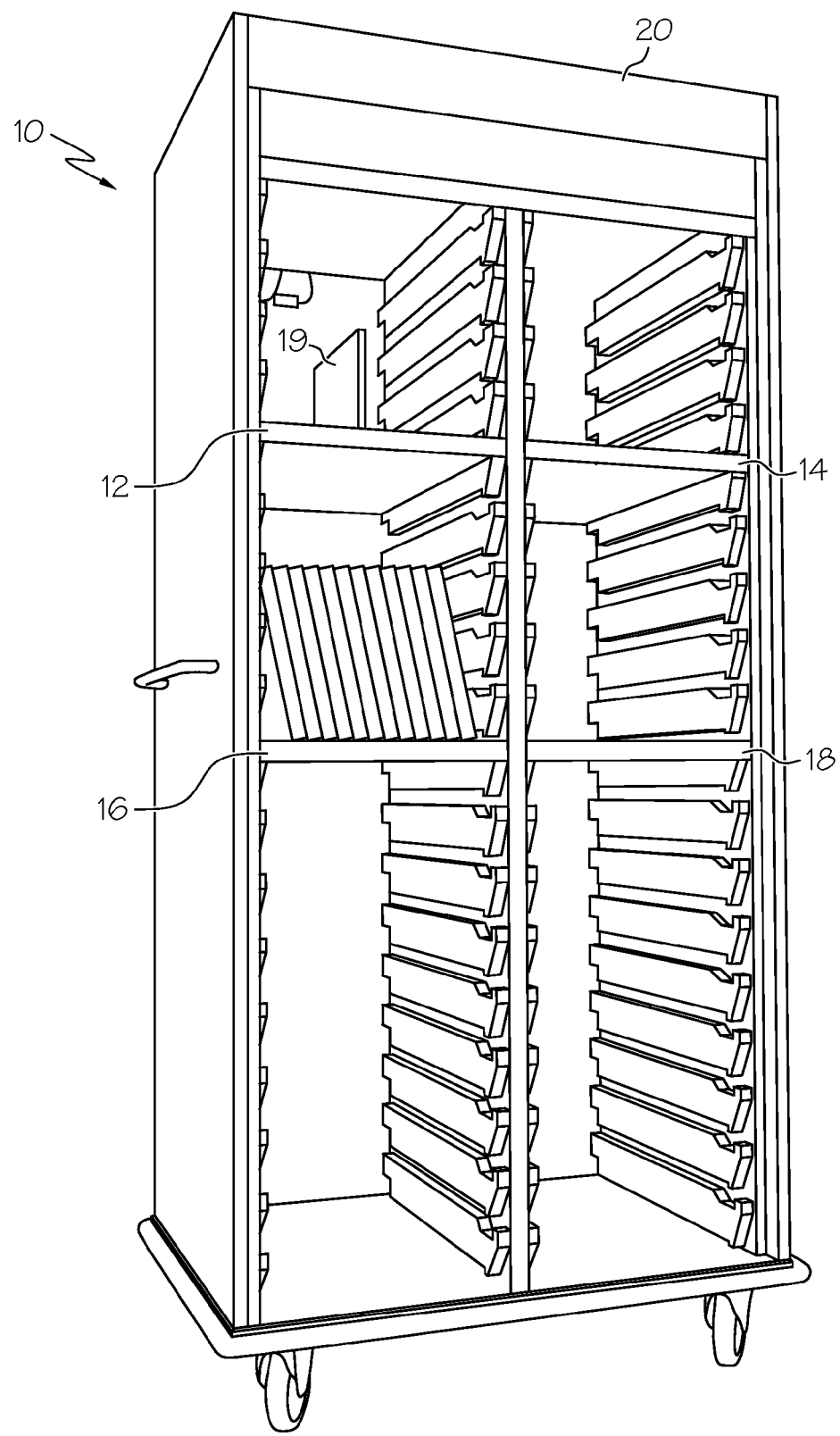
FIG. 1 shows a cabinet.

An antenna assembly constructed in accordance with the current embodiment of the invention is illustrated in the drawings as well as shelves containing the antenna assembly and a cabinet for use with the shelves.

A cabinet 10 for holding a variety of different sized articles is show in FIG. 1. The cabinet 10 includes several repositionable shelves 12, 14, 16, 18. The shelves 12, 14, 16, 18 can be positioned at various locations within cabinet 10. A divider 19 can also be located in the middle of a shelf. Alternatively, multiple dividers could be used on a shelf.

The antenna assemblies described hereinafter may be placed within the shelves 12, 14, 16, 18 and the divider 19, thereby allowing an RFID reader to read the RFID tags of articles placed within cabinet 10.

Various electronic devices associated with reading RFID tags can be placed within the top 20 of the cabinet 10. For example, a switch, an RFID reader and a processor can be placed within the top 20 of the cabinet 10 in order to facilitate the use of the shelves 12, 14, 16, 18 with an antenna assembly for reading RFID tagged articles contained within the cabinet 10.

Figure 2:
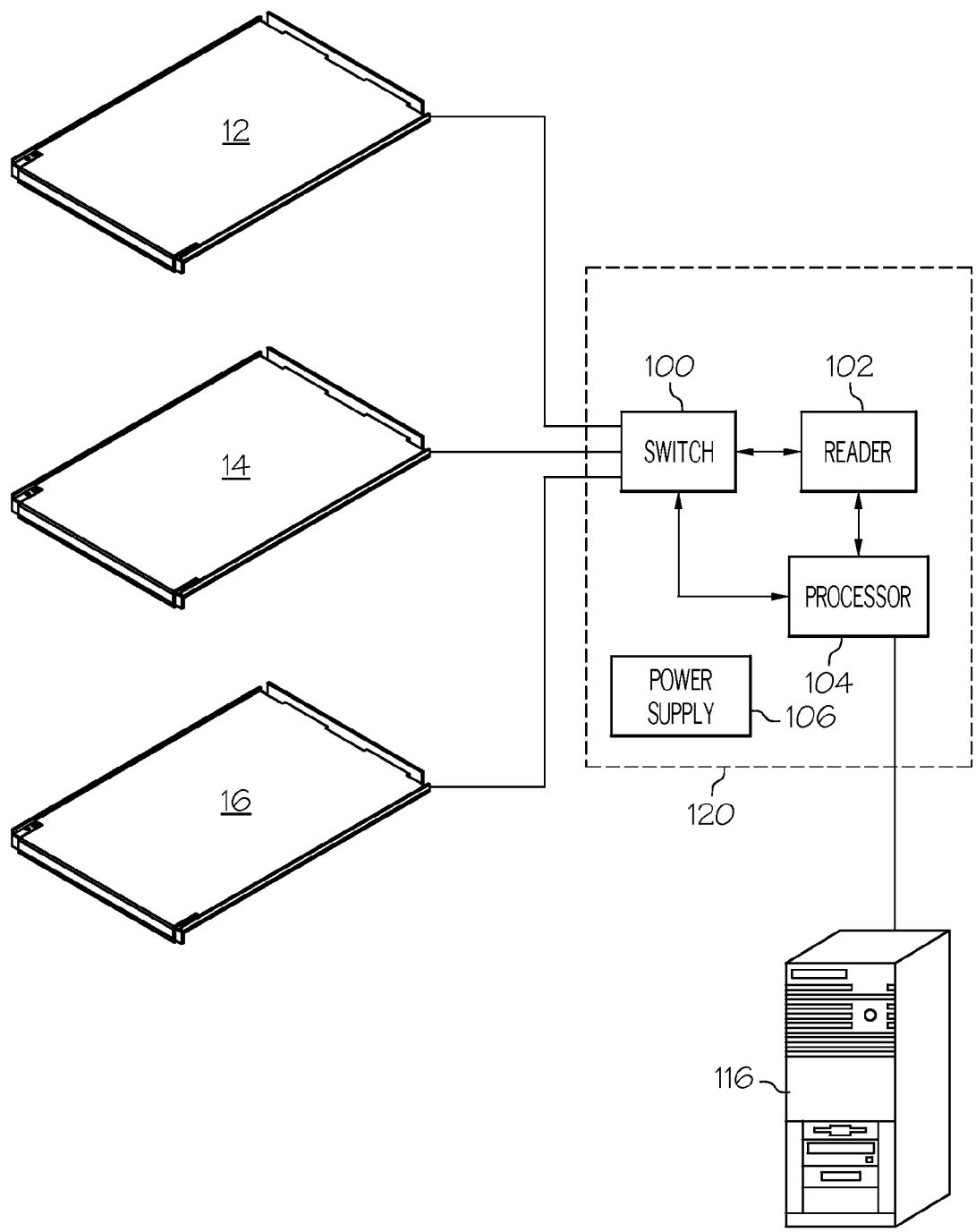
FIG. 2 shows an RFID reader system.

FIG. 2 shows the RFID reader system. The switches within the shelves 12, 14, 16 are multiplexed by way of the switch 100 with the reader 102. Switches within the shelves 12, 14, 16 and switch 100 are used to sequentially allow the reader 102 to read each antenna within the shelves. The reader 102 reads one antenna at a time, and then provides information regarding the RFID tags found by that antenna to processor 104. The processor 104 maintains a list of all items found on each shelf and compiles a list of the contents of the cabinet 10. It then relays that information to the server 116. The server 116 could be coupled to multiple cabinets similar to that shown in FIG. 1. If so, then the server 116 could have a database showing the location of all items contained within the cabinets.

The switch 100, the reader 102, and the processor 104 can be located in the top 20 of the cabinet 10. A power supply 106 located in the top 20 of the cabinet 10 provides power to the antenna assemblies within the shelves 12, 14, 16, thereby allowing the cabinet 10 to be moved as needed. The link between processor 104 and server 116 could be a wired link or a wireless link. If a wireless link is used, then the cabinet 10 could be quickly and easily positioned without regard to the location of a wired data communication port, further enhancing the adaptability of the cabinet 10.

The server 116 references a database and matches the RFID tags to specific items, thereby allowing server 116 to keep an accurate inventory as to the quantity and location of various items within an entire facility.

Figure 3:
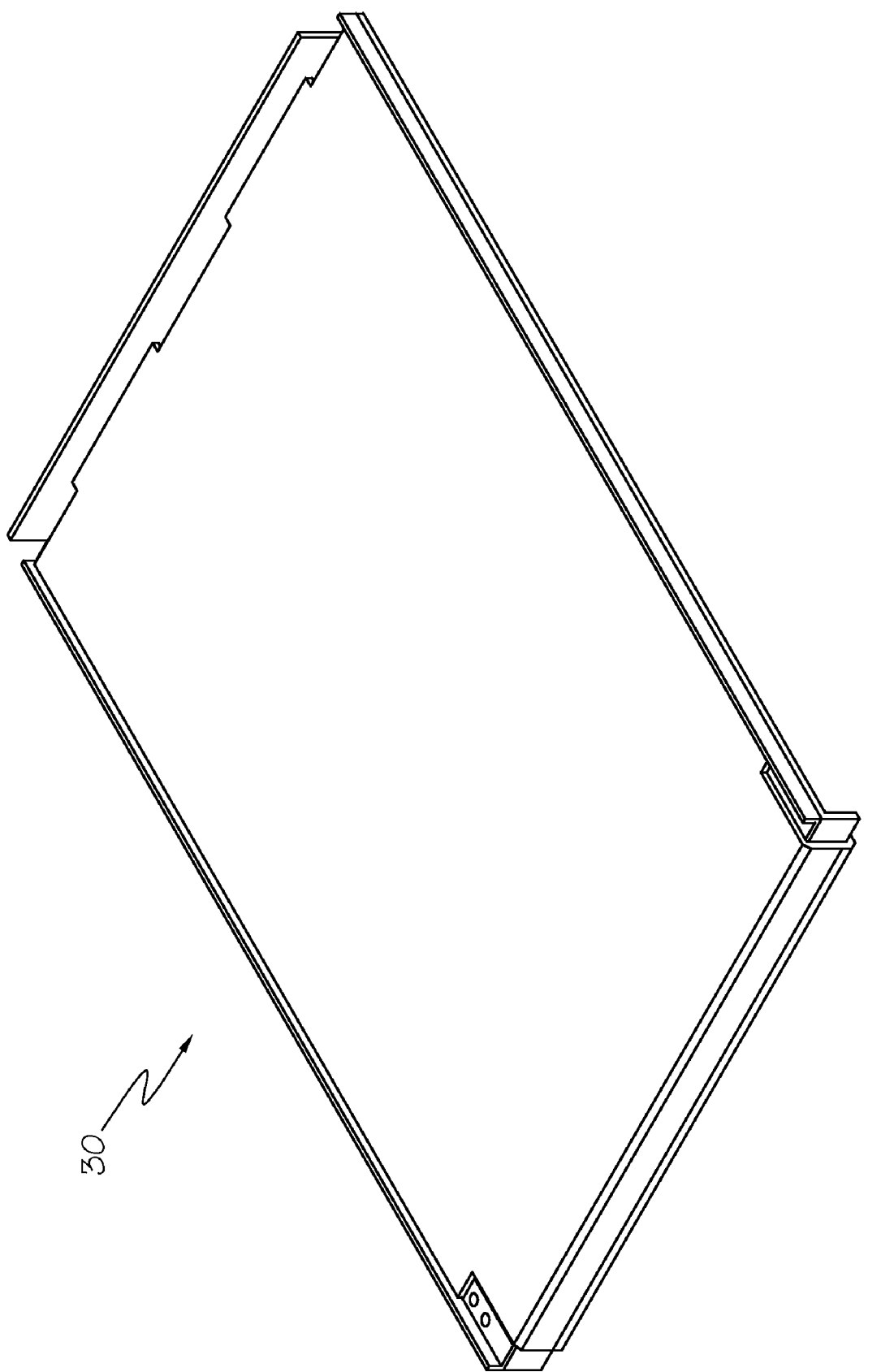
FIG. 3 shows an exemplary shelf within the cabinet of FIG. 2.
Figure 4:
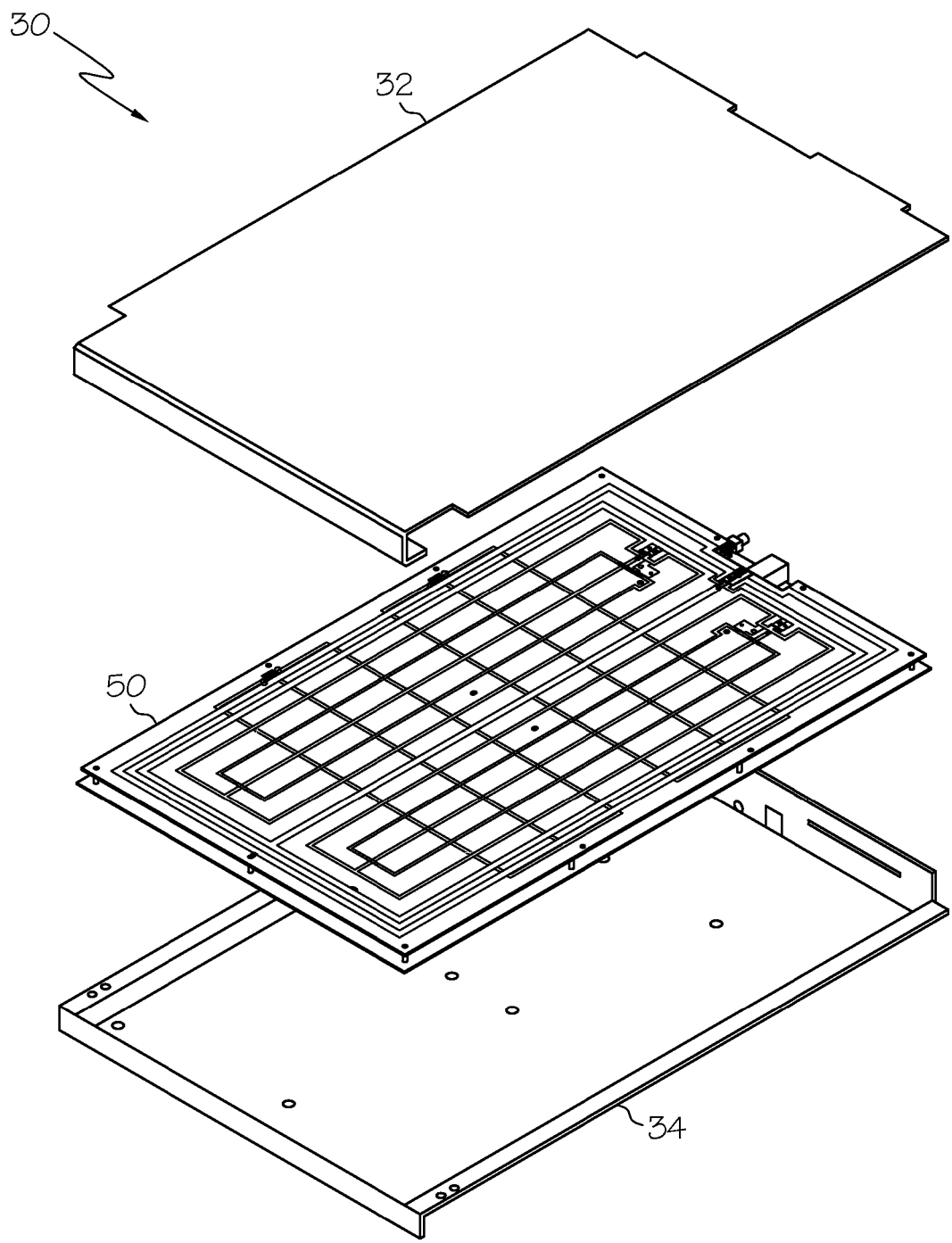
FIG. 4 is an exploded view of shelf.

FIG. 3 shows an exemplary shelf 30 for the cabinet 10 shown in FIG. 1, while FIG. 4 is an exploded view of the shelf 30. The shelf 30 includes a top 32, a bottom 34, and an antenna assembly 50. By enclosing the antenna assembly in the shelf 30, the antenna assembly 50 is able to read the RFID tags of articles placed on the shelf 30. The provision of antennas in different orientations within the antenna assembly 50 compensates for situations where articles are placed on the shelves such that the RFID tags are not optimally aligned with any one antenna.

Figure 5:
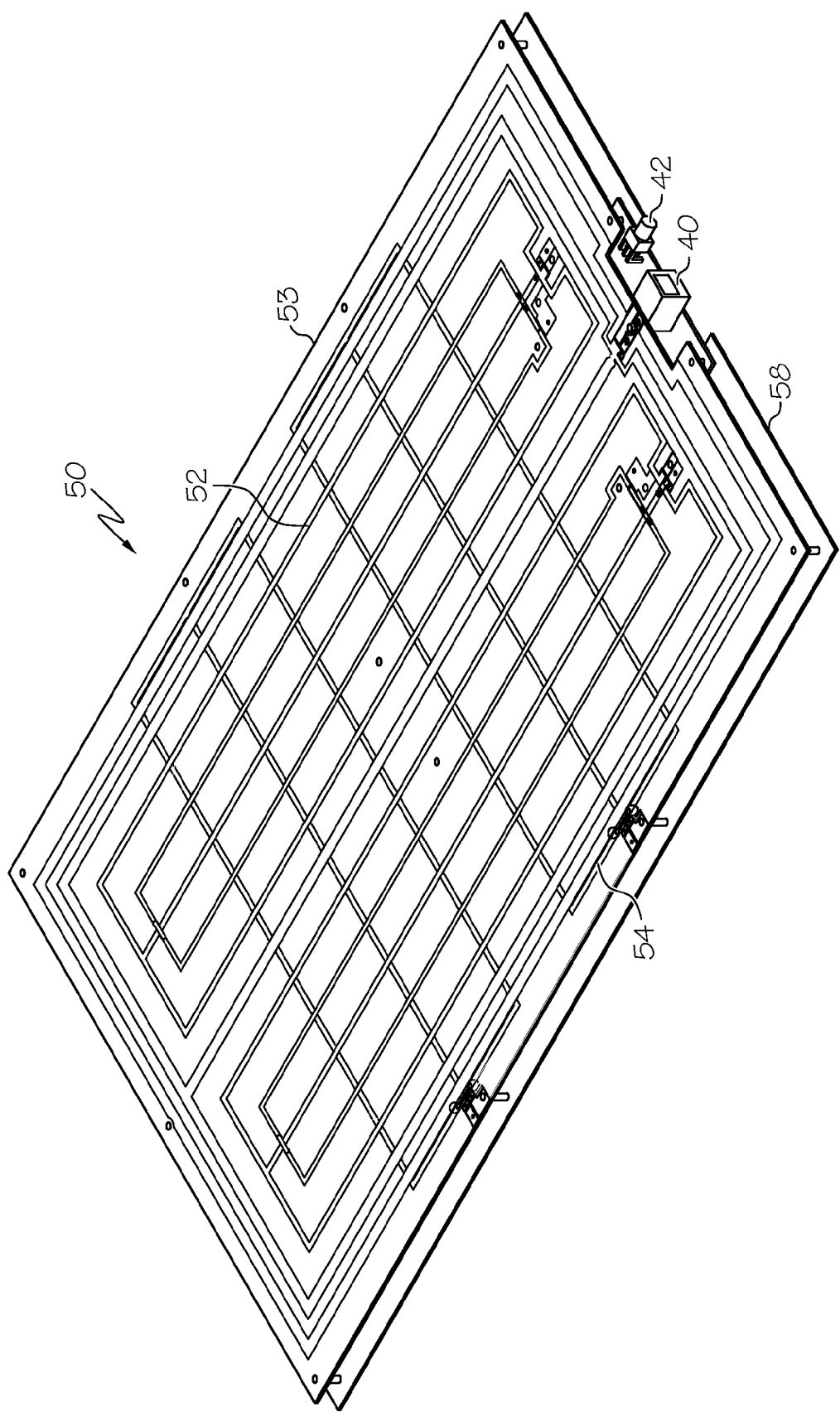
FIG. 5 is a perspective view of antenna assembly.
Figure 6:
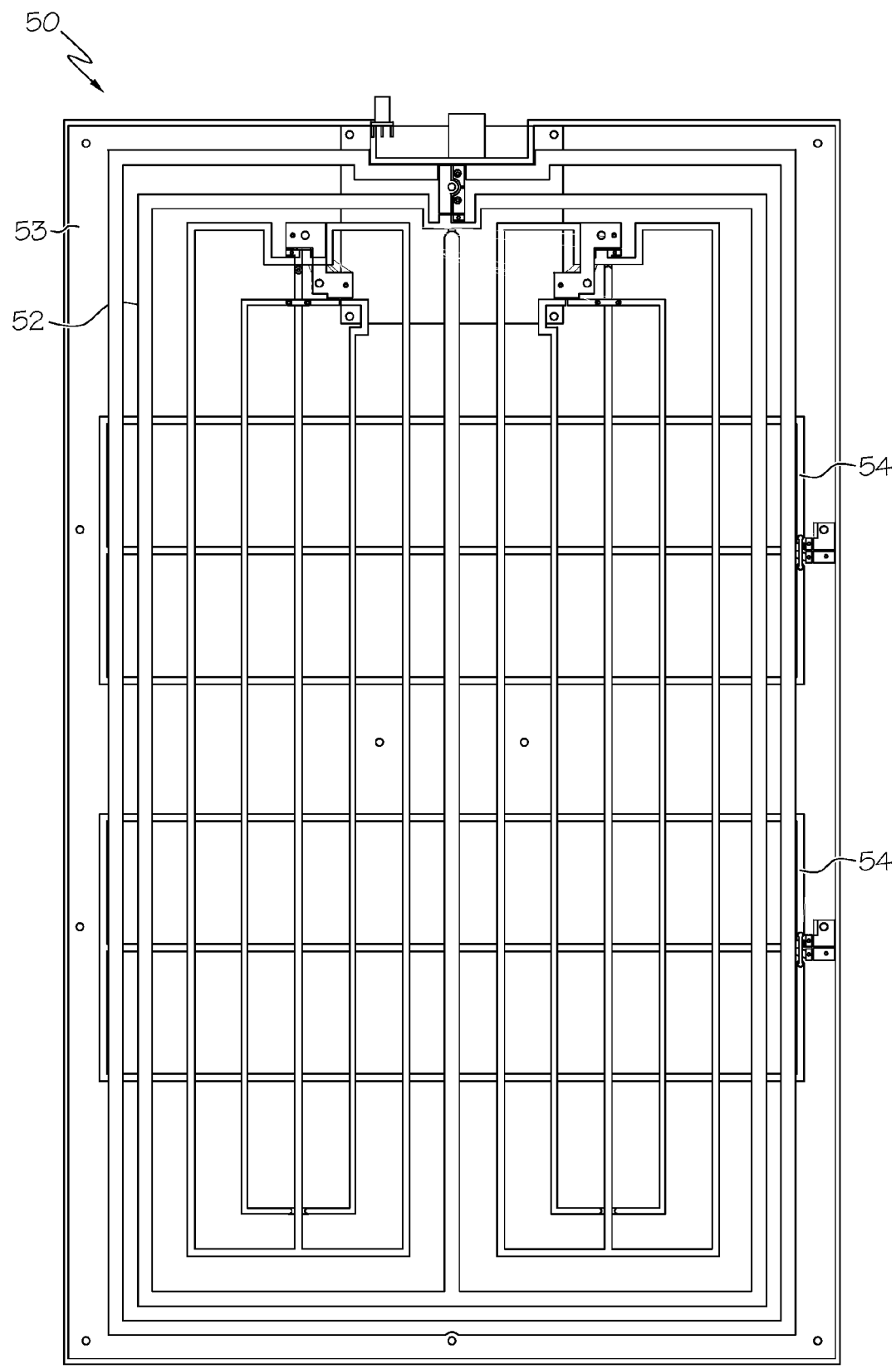
FIG. 6 is a top view of the antenna assembly shown in FIG. 5.
Figure 7:
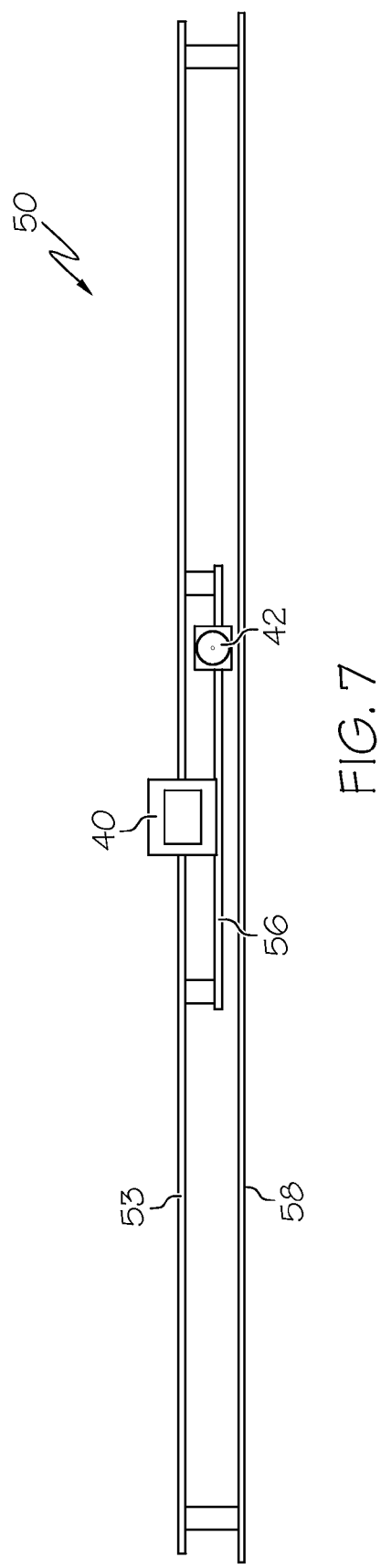
FIG. 7 is a side view of the antenna assembly shown in FIG. 5.

The antenna assembly 50 is shown in different views in FIGS. 5, 6 and 7. FIG. 5 is a perspective view of antenna assembly 50, while FIG. 6 is a top view of antenna assembly 50. FIG. 7 is a side view of antenna assembly 50.

The antenna assembly 50 includes multiple antennas located within a first antenna layer 52 and a second antenna layer 54. A switch 56, such as, for example, a single pole eight throw switch, reads each antenna within the antenna layers 52, 54. The switch 56 is connected to the RJ45 connector 40 and the RF connector 42. The switch 56 is located between the PC board 53 and the backplane 58. The switch 56 periodically and sequentially scans the various antennas within the antenna assembly 50 and provides the results of the scanning through the RJ45 connector 40 to a processor.

It would be possible to route the RF signal through the RJ45 connector 40, thereby eliminating the need for the RF connector 42. As is well known, a CAT5 cable includes several twisted pairs. One or more of the twisted pairs could be used as a transmission medium to carry the RF signals from the various antennas. If so, then the installation and movement of the shelves within the cabinet 10 would be further simplified since only a single connector would need to be attached or detached if the shelf were to be moved.

The first antenna layer 52 is on the top side of the PC board 53. The second antenna layer 54 is on the bottom side of the PC board 53. The PC board 53 is translucent, thereby allowing an observer to see both the first antenna layer 52 and the second antenna layer 54.

Figure 8:
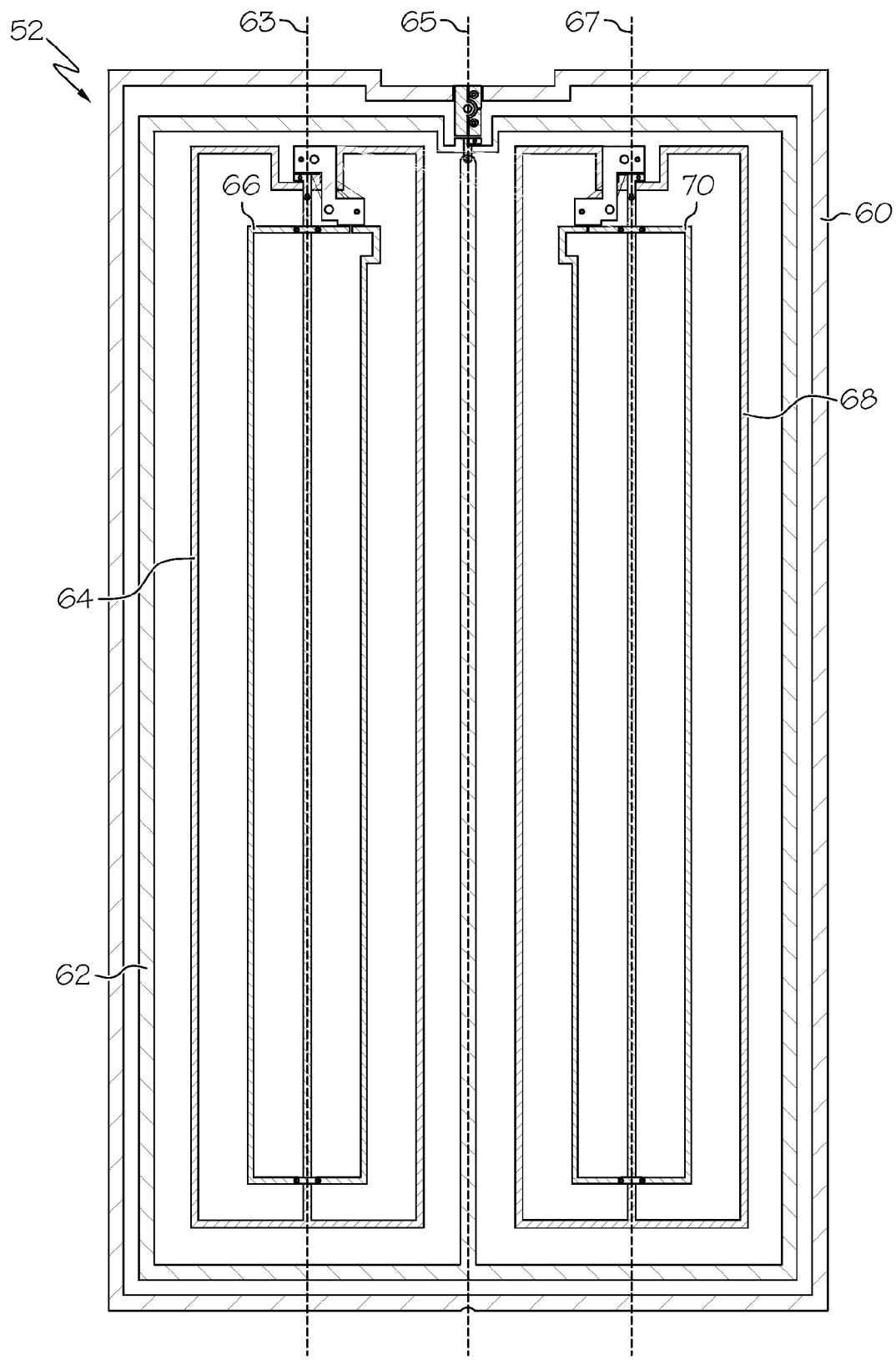
FIG. 8 shows a first antenna layer of the antenna assembly.

FIG. 8 shows the first antenna layer 52. The first antenna layer 52 is comprised of a first loop antenna 60, a first figure eight antenna 62, a second figure eight antenna 64, a second loop antenna 66, a third figure eight antenna 68, and a third loop antenna 70.

The first loop antenna 60 and the first figure eight antenna 62 extend along an axis 65, hereinafter referred to generally as the X-axis. The second figure eight antenna 64 and the second loop antenna 66 extend along an axis 63. Third figure eight antenna 68 and third loop antenna 70 extend along axis 67. The axes 63, 67 are parallel to the X-axis 65.

The first figure eight antenna 62 is within the perimeter of the first loop antenna 60. The second loop antenna 66 is within the perimeter of the second figure eight antenna 64, while the third figure eight antenna 68 contains the third loop antenna 70.

The antennas within the first antenna layer 52 are generally within the same plane and are fabricated on the top of the PC board 53. It would be possible to have portions of the antennas extend from the top of the PC board 53.

If coupling occurs between the first loop antenna 60 and the first figure eight antenna 62, any currents produced by the coupling will be offset by equal and opposite currents. For example, if coupling occurred between the first loop antenna 60 and a portion of the first figure eight antenna 62, then a current of equal magnitude but opposite direction would occur in the a portion of the first figure eight antenna on the opposite side of axis 63. The two currents would thus cancel out, mitigating the effect of the coupling between the two antennas.

Similarly, if coupling created currents in the first loop antenna 60 by a portion of the first figure eight antenna 62, then an opposite but equal current would also be created in a portion of the first loop antenna 60 on the opposite side of axis 63. The effects of the coupling are thereby substantially reduced.

By substantially reducing the coupling between the first loop antenna 60 and the first figure eight antenna 62, a high degree of isolation between the first loop antenna 60 and the first figure eight antenna 62 can be achieved. Antenna isolation of at least 20 dB and even 30 dB can be achieved between the first figure eight antenna 62 and the first loop antenna 60. This isolation is accomplished through minimal use of tuning capacitors.

The first loop antenna 60 and the first figure eight antenna 62 form an antenna pair. The second figure eight antenna 64 and second figure loop antenna 66 form an additional antenna pair, while third figure eight antenna 68 and third loop antenna 70 form yet another antenna pair. Each of the antenna pairs consist of a loop antenna with a figure eight antenna. The loop antenna for each antenna pair is slightly larger than the figure eight antenna.

In order to simplify the manufacture of the antenna assembly, each antenna with each antenna pair have antenna elements of approximately the same width. However, the antenna elements within different antenna pairs may differ in order to simplify the fabrication of the antenna assembly.

As can be seen by inspection of the figures, the conductive material needed to form the first figure eight antenna 62 is significantly longer than the material for the second figure eight antenna 64. Therefore, if the first figure eight antenna 62 were made from identical material having the same width as the material forming second figure antenna 64, then the inductance of the first figure eight antenna 62 would be significantly different from that of the second figure eight antenna 64, thereby requiring different sizes of tuning capacitors for each antenna. However, by having the antenna elements of the first figure eight antenna 62 wider than the antenna elements of the second figure eight antenna 64, the inductance of the first figure eight antenna 62 and the second figure eight antenna 64 is such that tuning capacitors of the same size can be used for each antenna. Using the same size tuning capacitors for the first figure eight antenna 62 and the second figure eight antenna 64 reduces the complexity and thereby the cost of manufacturing the entire antenna assembly.

Therefore, the antenna elements of the antennas 60, 62 are wider than the antenna elements of the antennas 64, 66, 68, 70, while the widths of the antenna elements for the antennas 64, 66, 68, and 70 are approximately the same. The inductance of the antennas 60, 62, 64, 66, 68 70 is approximately the same, allowing the use of similar tuning capacitors for each antenna, and thereby reducing the cost of manufacturing the entire antenna assembly.

The first antenna layer 52 reads RFID tags in most orientations. However, to further improve the coverage, a second antenna layer 54 is used. The second antenna layer 54 has antennas which are generally orthogonal to the first antenna layer 52.

Figure 9:
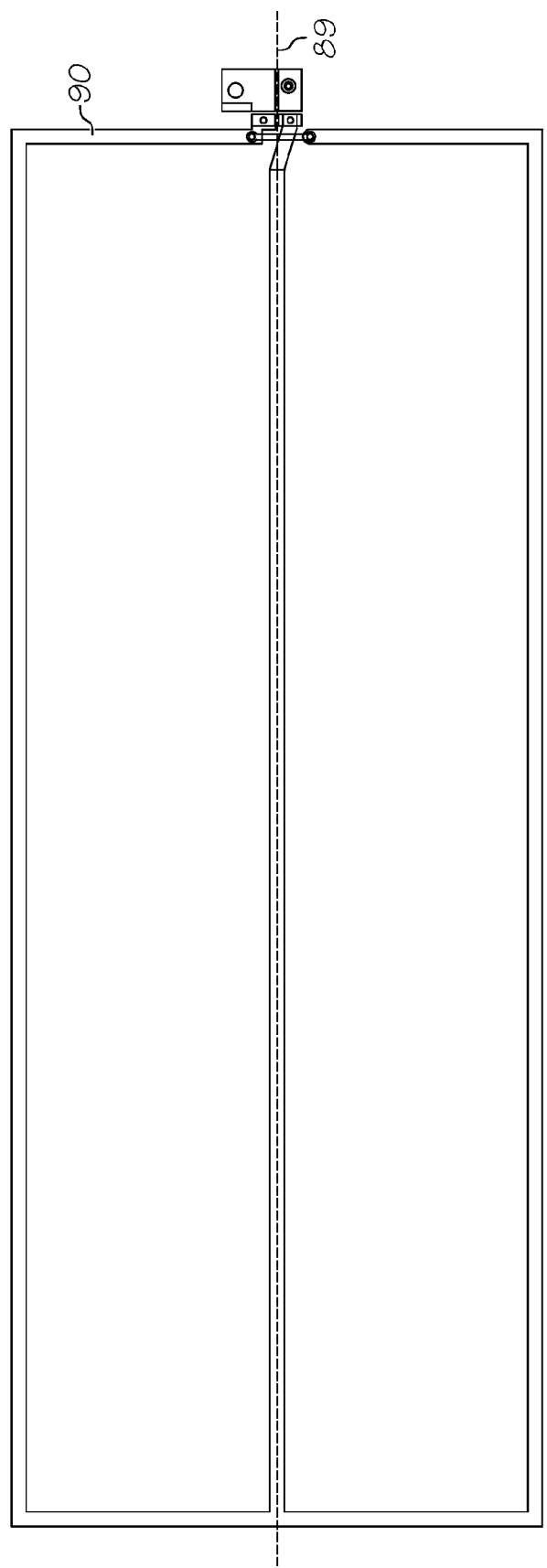
FIG. 9 shows one antenna from the second antenna layer.

FIG. 9 shows one antenna 90 from the second antenna layer 54. The antenna 90 is a figure eight antenna. The antenna 90 extends along axis 89, referred to as the Y-axis 89. The second antenna layer 54 is positioned so that the antennas within that antenna layer are aligned generally perpendicular to the X-axis 65 of the antennas within the first antenna layer 52. The second antenna layer allows reading of RFID tags which are generally perpendicular to the X-axis 65 but parallel to the Y-axis 89. The antennas within the second antenna layer 54 are also generally within a single plane.

Figure 10:
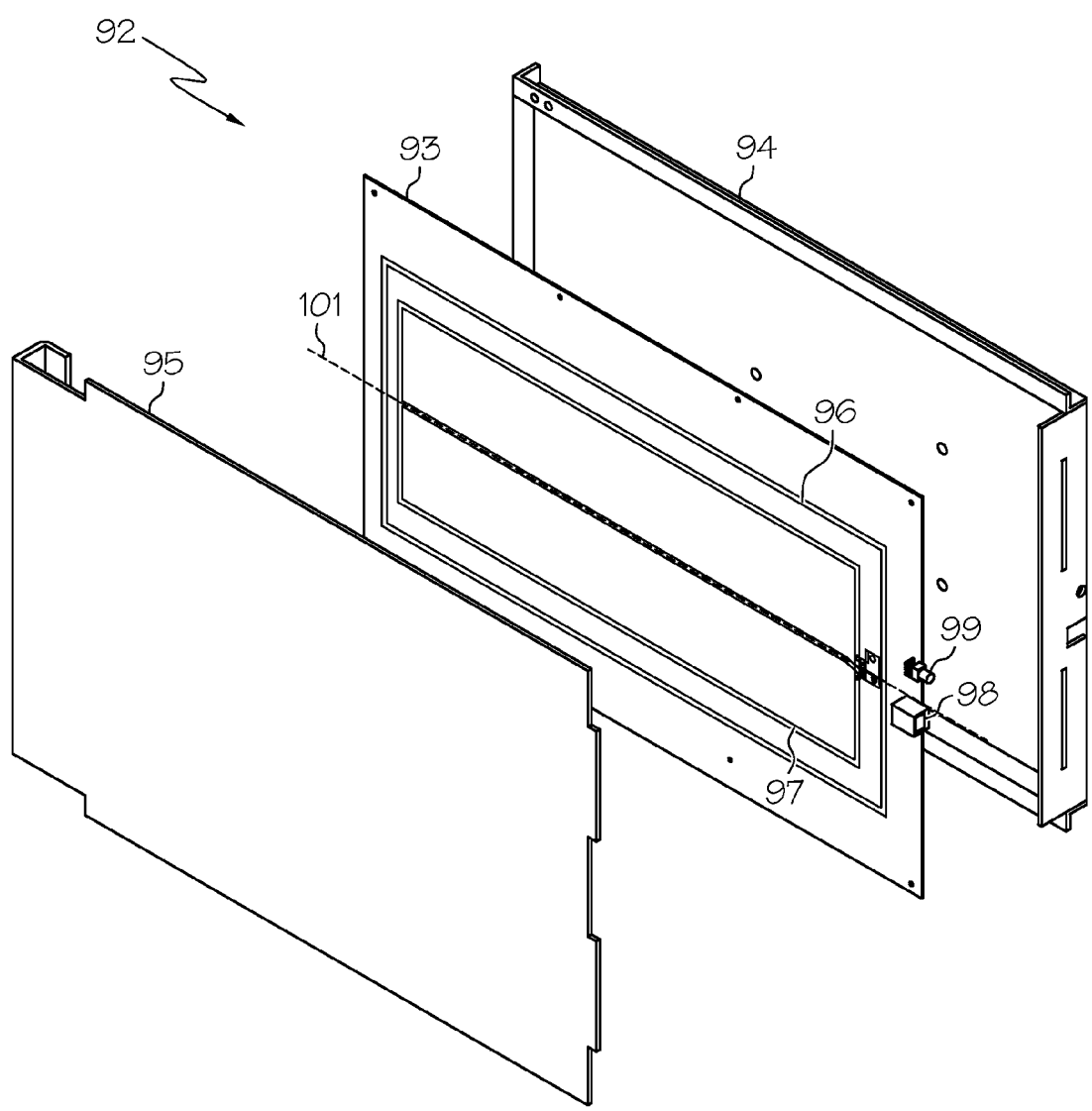
FIG. 10 is an exploded view of divider for use with the shelf shown in FIG. 3.

FIG. 10 shows a divider 92. The divider 92 includes an antenna assembly 93 between an enclosure formed by the sidewall 94 and the sidewall 95. The sidewalls 94, 95 are preferably plastic or some other type of material which does not hinder the operation of the antenna assembly 93. The antenna assembly 93 includes a loop antenna 96 surrounding a figure eight antenna 97. The loop antenna 96 and the figure eight antenna 97 extend along the axis 101. The axis 101 is generally parallel to the X-axis 65, but generally perpendicular to the Y-axis 89.

The RF connector 98 routes RF to the antenna assembly 93 from the reader by way of a coaxial cable, while the RJ45 connector 99 allows the digital control logic connection to the processor via a CAT5 cable. One or more of the twisted pairs from the CAT5 cable could be used as a transmission medium to carry the RF signals from the various antennas within the antenna assembly 93.

The divider 92 is moveable, and is placed vertically on a shelf so that the antennas extend along an axis parallel to the shelf and perpendicular to the back of the cabinet.

The above description is that of the current embodiment of the invention. Various alterations and changes can be made without departing from the spirit and broader aspects of the invention as defined in the appended claims, which are to be interpreted in accordance with the principles of patent law including the doctrine of equivalents.

The embodiments of the invention in which an exclusive property or privilege is claimed are defined as follows:

1. A system for tracking articles having RFID tags within a cabinet comprising:
   a repositionable shelf having a first antenna assembly, the repositionable shelf extending generally horizontally, the repositionable shelf having a power input and a data connector, the data connector for connection to an RFID reader; and
   a divider having a second antenna assembly, the divider extending generally vertically, the divider having a power input and a data connector, the data connector for connection to the RFID reader.

2. The system of claim 1 where the divider is repositionable.

3. The system of claim 2 further where the first antenna assembly has a first antenna pair in a shelf plane, and the second antenna assembly has a second antenna pair in a divider plane, and the shelf plane is perpendicular to the divider plane.

4. The system of claim 3 where the first antenna pair extend along a first antenna pair axis, the second antenna pair extend along a second antenna pair axis, and the first antenna assembly includes a first antenna extending along an first antenna axis, the first antenna axis being generally perpendicular to the first antenna pair axis and the second antenna pair axis.

5. The system of claim 4 where the first antenna assembly includes a third antenna pair, the third antenna pair being generally coplanar with the first antenna pair.

6. The system of claim 5 where the first antenna assembly includes a fourth antenna pair, the fourth antenna pair being generally coplanar with the first antenna pair.

7. The system of claim 6 further comprising a second antenna coplanar with the first antenna.

8. The system of claim 7 where the first antenna pair comprise a first loop antenna and a first figure eight antenna.

9. The system of claim 8 where the second antenna pair comprise a second loop antenna and a second figure eight antenna.

10. The system of claim 9 where the first antenna is a loop antenna and the second antenna is a figure eight antenna.

* * * * *